(12) United States Patent
Kaminsky et al.

(10) Patent No.: US 11,918,501 B2
(45) Date of Patent: *Mar. 5, 2024

(54) DYNAMIC ARM BRACE ASSEMBLIES AND METHODS OF USE

(71) Applicants: Sean Kaminsky, Nashville, TN (US); John M. Behles, Bixby, OK (US); Ian Kovacevich, Carlsbad, CA (US)

(72) Inventors: Sean Kaminsky, Nashville, TN (US); John M. Behles, Bixby, OK (US); Ian Kovacevich, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/589,115

(22) Filed: Jan. 31, 2022

(65) Prior Publication Data

US 2022/0287863 A1 Sep. 15, 2022

Related U.S. Application Data

(63) Continuation of application No. 15/705,184, filed on Sep. 14, 2017, now Pat. No. 11,234,851.

(Continued)

(51) Int. Cl.
*A61F 5/01* (2006.01)
*A61F 5/37* (2006.01)

(52) U.S. Cl.
CPC .............. *A61F 5/013* (2013.01); *A61F 5/01* (2013.01); *A61F 5/373* (2013.01); *A61F 5/3738* (2013.01);
(Continued)

(58) Field of Classification Search
CPC ........ A61F 5/01; A61F 5/0118; A61F 5/0125; A61F 5/013; A61F 5/3715; A61F 5/3723; A61F 5/373; A61F 5/3738; A61F 5/3753; A61F 5/37; A61F 5/3728; A61F 5/3746; A61F 5/3761; A61F 5/0102;
(Continued)

(56) References Cited

U.S. PATENT DOCUMENTS 5,665,058 A 9/1997 Young
2004/0215119 A1* 10/2004 Avon .................... A61F 5/3738
602/4

(Continued)

OTHER PUBLICATIONS

International Preliminary Report on Patentability from PCT Application No. PCT/US2017/051322 dated Dec. 28, 2017, 7 pages.
(Continued)

*Primary Examiner* — Alireza Nia
*Assistant Examiner* — Daniel A Miller

(57) ABSTRACT

Dynamic arm brace assemblies and methods of use are provided herein. An example device includes a torso connection member securable to a torso of a patient, a forearm support member that couples with at least a forearm of an patient, the forearm support member couples with the torso connection member so as to fix an elbow of the patient proximate the torso, the forearm support member being pivotally coupled to the torso connection member to allow for an angle between the forearm support member and a coronal plane of the patient, and a dynamic tensioning assembly that externally rotates the forearm support member and selectively sets the angle so as to stretch a shoulder capsule (capsule and adjacent tissue(s)) affected with adhesive capsulitis, reducing the adhesive capsulitis.

9 Claims, 15 Drawing Sheets

Related U.S. Application Data

(60) Provisional application No. 62/394,548, filed on Sep. 14, 2016.

(52) U.S. Cl.
CPC ............. *A61F 2005/0151* (2013.01); *A61F 2005/0153* (2013.01); *A61F 2005/0158* (2013.01); *A61F 2005/0167* (2013.01); *A61F 2005/0179* (2013.01)

(58) Field of Classification Search
CPC .. A61F 5/0104; A61F 5/04; A61F 5/05; A61F 5/0123; A61F 5/0585; A61F 5/05858; A61F 5/05866; A61F 2005/0139; A61F 2005/0151; A61F 2005/0153; A61F 2005/0158; A61F 2005/0167; A61F 2005/0169; A61F 2005/0179; A61F 2005/0132; A61F 2/50; A61H 2201/1635
USPC .......................................................... 602/16
See application file for complete search history.

(56) References Cited

U.S. PATENT DOCUMENTS

| | | | |
|---|---|---|---|
| 2008/0228118 A1* | 9/2008 | Bull | A61F 5/3723 602/16 |
| 2013/0110020 A1 | 5/2013 | Ingimundarson et al. | |
| 2014/0371644 A1* | 12/2014 | Erbe | A61F 5/3753 602/4 |
| 2015/0150711 A1* | 6/2015 | Van De Ven | A61F 5/055 602/18 |
| 2016/0038368 A1 | 2/2016 | Lee et al. | |
| 2016/0199231 A1* | 7/2016 | Capra | A61F 5/0111 602/12 |
| 2016/0256311 A1* | 9/2016 | Lemmon | A61F 5/3738 |

OTHER PUBLICATIONS

International Search Report and Written Opinion from PCT Application No. PCT/US2017/051322 dated Mar. 19, 2019, 6 pages.

\* cited by examiner

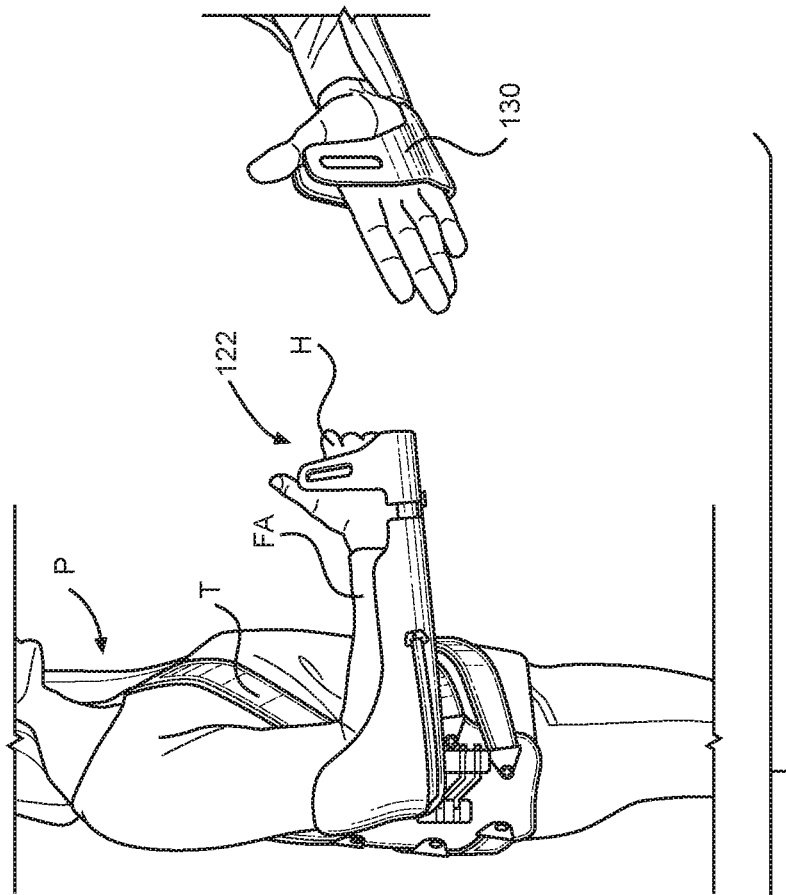
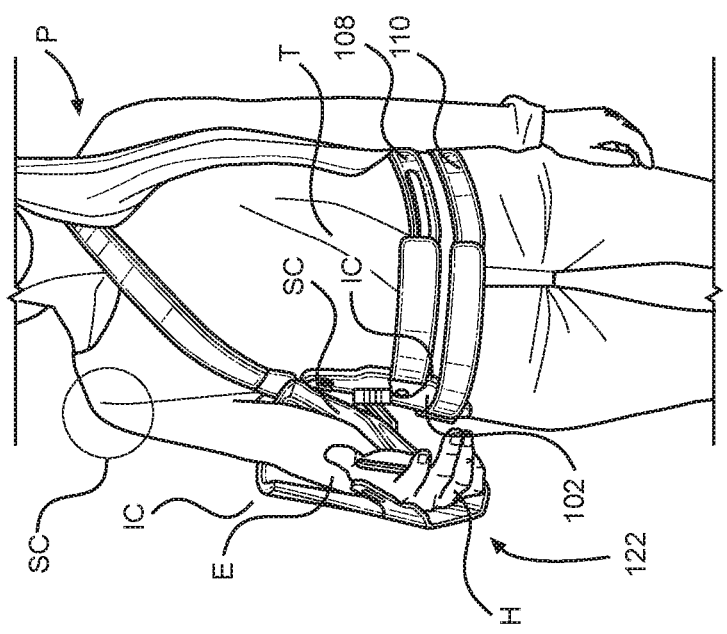
FIG. 1B

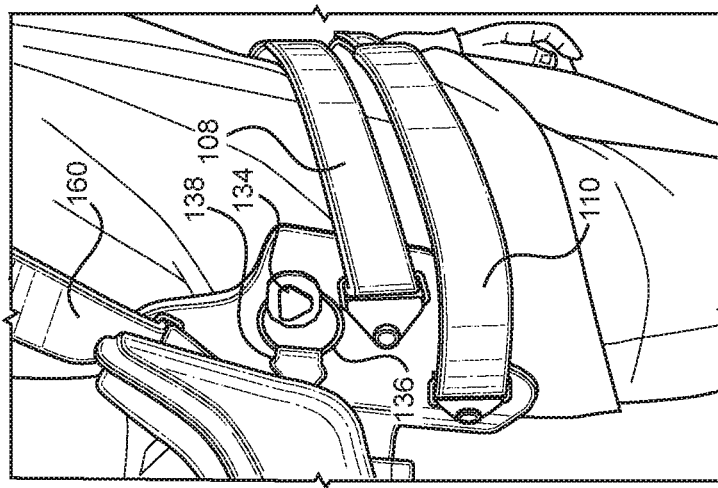
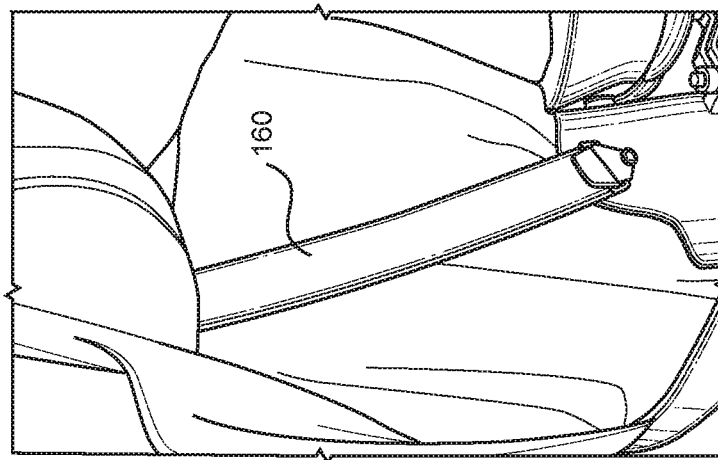
FIG. 1C

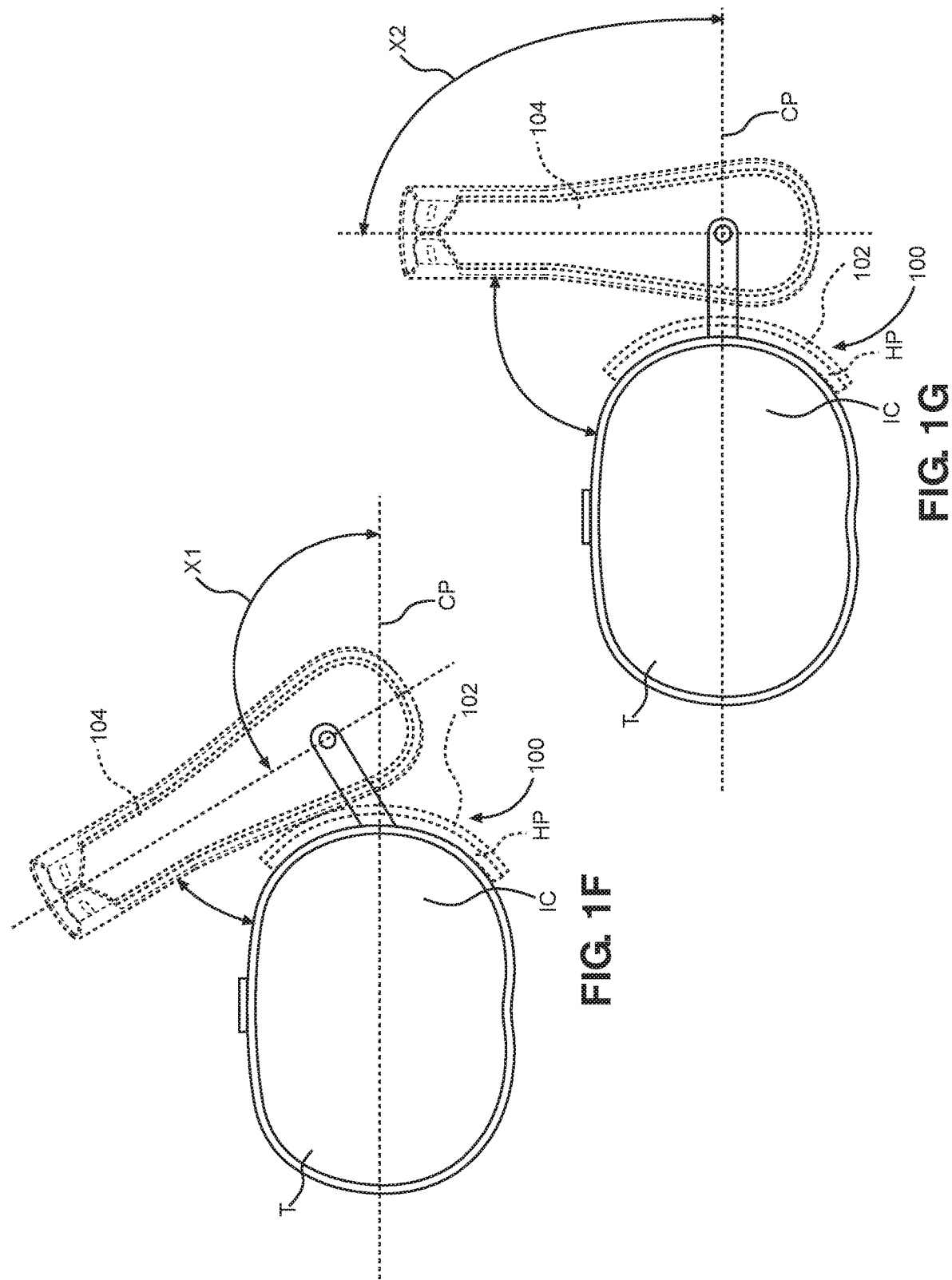

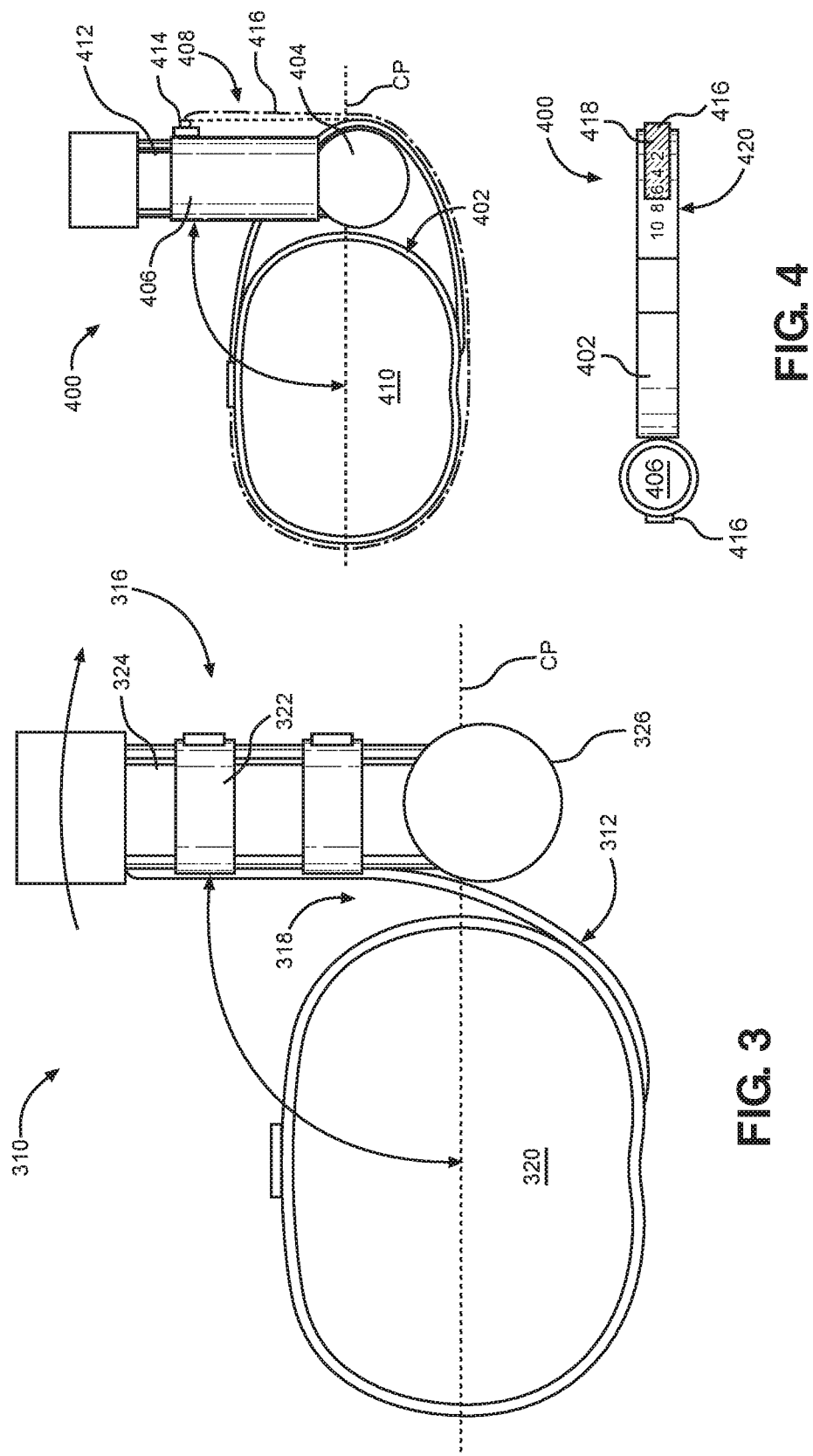

DYNAMIC ARM BRACE ASSEMBLIES AND METHODS OF USE

CROSS REFERENCE TO RELATED APPLICATIONS

This application is a continuation of U.S. application Ser. No. 15/705,184, filed on Sep. 14, 2017, which claims the benefit and priority of U.S. Provisional Application Ser. No. 62/394,548, filed on Sep. 14, 2016, which are hereby incorporated by reference in their entireties for all purposes, including all references and appendices cited therein.

FIELD OF INVENTION

The present disclosure relates generally to orthopedic braces and more particularly, but not by limitation to arm brace assemblies that cause external rotation of a forearm of an patient to position the shoulder in an adducted (or neutral) position for optimal healing and recovery from injury or surgery. In some embodiments, the braces described herein improve mobility and reduce (stiffness, adhesions, loss of range-of-motion) or adhesive capsulitis in patients. The brace may include a system with detachable grips or handles to facilitate range-of-motion exercises with a formal and/or home exercise program.

SUMMARY

According to some embodiments, the present disclosure is directed to a device, comprising: (a) a torso connection member securable to a torso of the patient; (b) a forearm support member that couples with at least a forearm of an patient, wherein the forearm support member couples with the torso connection member so as to fix an elbow of the patient proximate the torso, the forearm support member being pivotally coupled to the torso connection member to allow for an angle between the forearm support member and a coronal plane of the patient; and (c) a dynamic tensioning assembly that externally rotates the forearm support member and selectively sets the angle so as to stretch a shoulder capsule affected with adhesive capsulitis so as to reduce the adhesive capsulitis.

According to some embodiments, the present disclosure is directed to a device comprising: (a) a forearm support member that secures to at least a forearm of an patient; (b) a torso connection member that is positioned and secure proximate an iliac crest of the patient; (c) wherein the forearm support member couples with the torso connection member in such a way that an elbow of the patient is proximate to a torso of the patient; and (d) wherein the forearm support member and a coronal plane of the patient can be placed approximately normal to one another using a dynamic tensioning assembly.

According to some embodiments, the present disclosure is directed to device comprising a support member that secures to at least a forearm of an patient and secures an elbow of the patient proximate a torso of the patient, wherein the support member is disposed at an angle measured by reference to a coronal plane of the patient, the angle being selectively adjusted using a dynamic tensioning member that causes external rotation of the forearm in order to stretch a shoulder capsule (shoulder capsule, joint, or soft-tissue) of a shoulder associated with the forearm.

According to some embodiments, the present disclosure is directed to device comprising (a) an arm brace comprising: (i) an elbow and upper arm retaining portion; (ii) a forearm retaining portion; (iii) an anchor location on an outside surface of the forearm retaining portion; (iv) a retaining slot located on a rearward portion of the elbow and upper arm retaining portion; and (v) an extendable, proximal grip disposed on a terminal end of the elbow and upper arm retaining portion, the extendable, proximal grip capable of sliding translation to adjust a length of the elbow and upper arm retaining portion, the extendable, proximal grip further comprising a pair of spaced apart hand grips; (b) a torso connection member comprising: (i) a body contoured to mate with a portion of a side of a torso of a patient at approximately an iliac crest of the patient; and (ii) one or more securement members coupled to the body, the one or more securement members configured to overlap an opposing side of the torso of the patient to secure the torso connection member on the torso; (c) a linkage that couples the elbow and upper arm retaining portion with the torso connection member in such a way that the an elbow of the patient is next to the torso of the patient, wherein the elbow and upper arm retaining portion is pivotally coupled with the linkage; (d) a dial tensioner that is disposed on a forward portion of the body so as to be reachable by an opposing hand of the patient that is not placed in the elbow and upper arm retaining portion; (e) a resilient strap that is coupled with the dial tensioner at one end, the resilient strap coupling with the forearm retaining portion using a clip that releasably connects with the anchor location, the resilient strap extending through the retaining slot; (f) wherein when the patient places their arm in the arm brace and rotates the dial tensioner, the arm brace pivots to externally rotate a forearm while the elbow is maintained in a fixed position, resulting in stretching of a shoulder capsule of a shoulder of the patient, the resilient strap providing a dynamic force that can be resisted against by the patient; and (g) a shoulder strap that overlaps a non-affected shoulder, the shoulder strap connected on both its ends to the body of the torso connection member.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

FIG. 1B illustrates both front elevation and side elevation views of the device of FIG. 1A on a patient.

FIG. 1C illustrates both a rear and side perspective views of the device of FIG. 1A.

FIG. 1F is a top down, partial view of the device of FIG. 1A showing an initial position proximate a torso of a patient.

FIG. 1G is a top down, partial view of the device of FIG. 1A showing an externally rotated forearm position of a patient.

FIG. 3 is a top-down perspective view of another embodiment of a device of the present disclosure.

FIG. 4 includes both a top-down perspective view of another embodiment of a device of the present disclosure, as well as a front elevation view thereof.

DETAILED DESCRIPTION OF EXAMPLE EMBODIMENTS

Figure 1A:
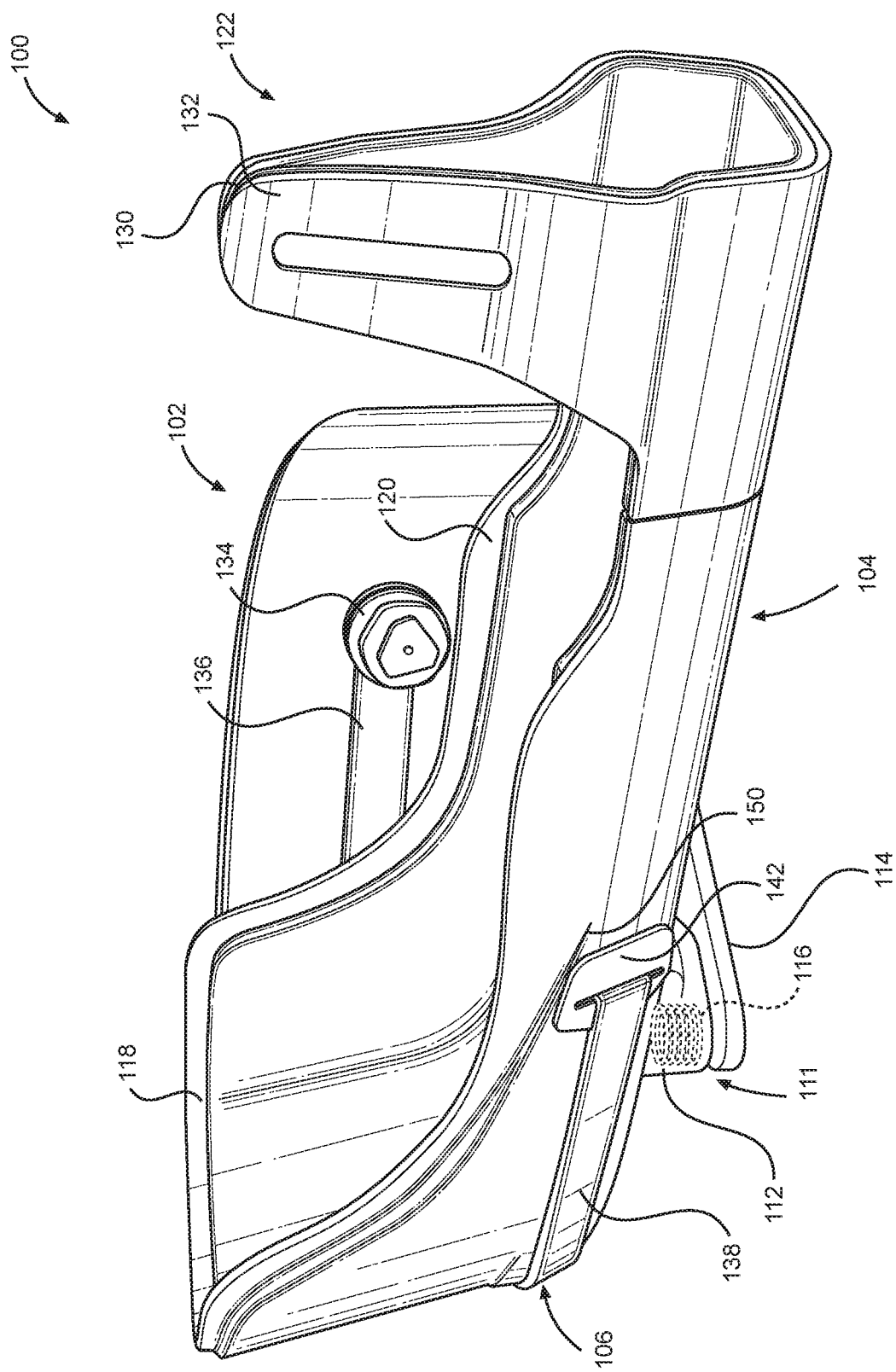
FIG. 1A is a perspective view of an example device, constructed in accordance with the present disclosure.
Figure 1D:
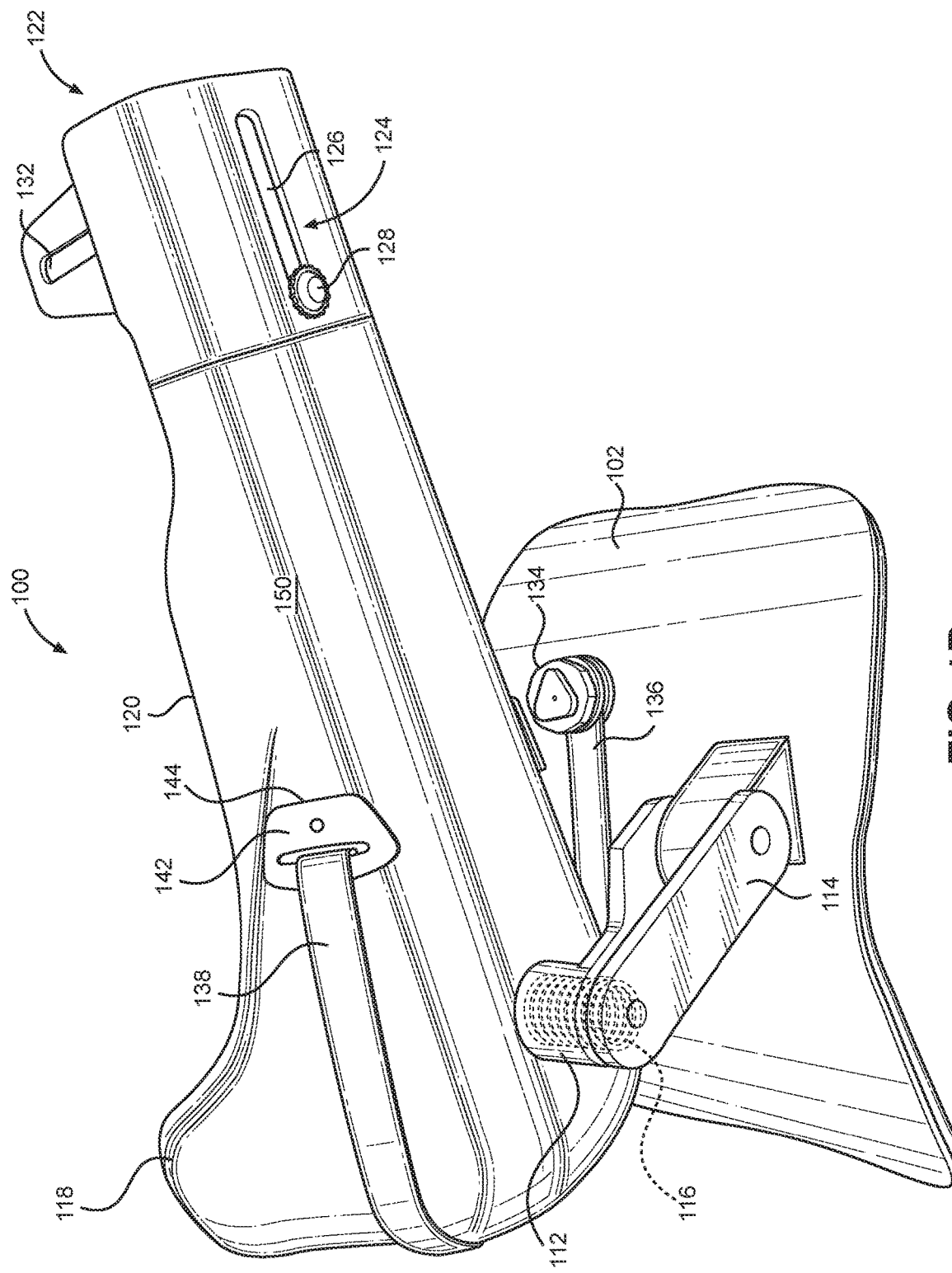
FIG. 1D is a bottom perspective view of the example device of FIG. 1A.
Figure 1E:
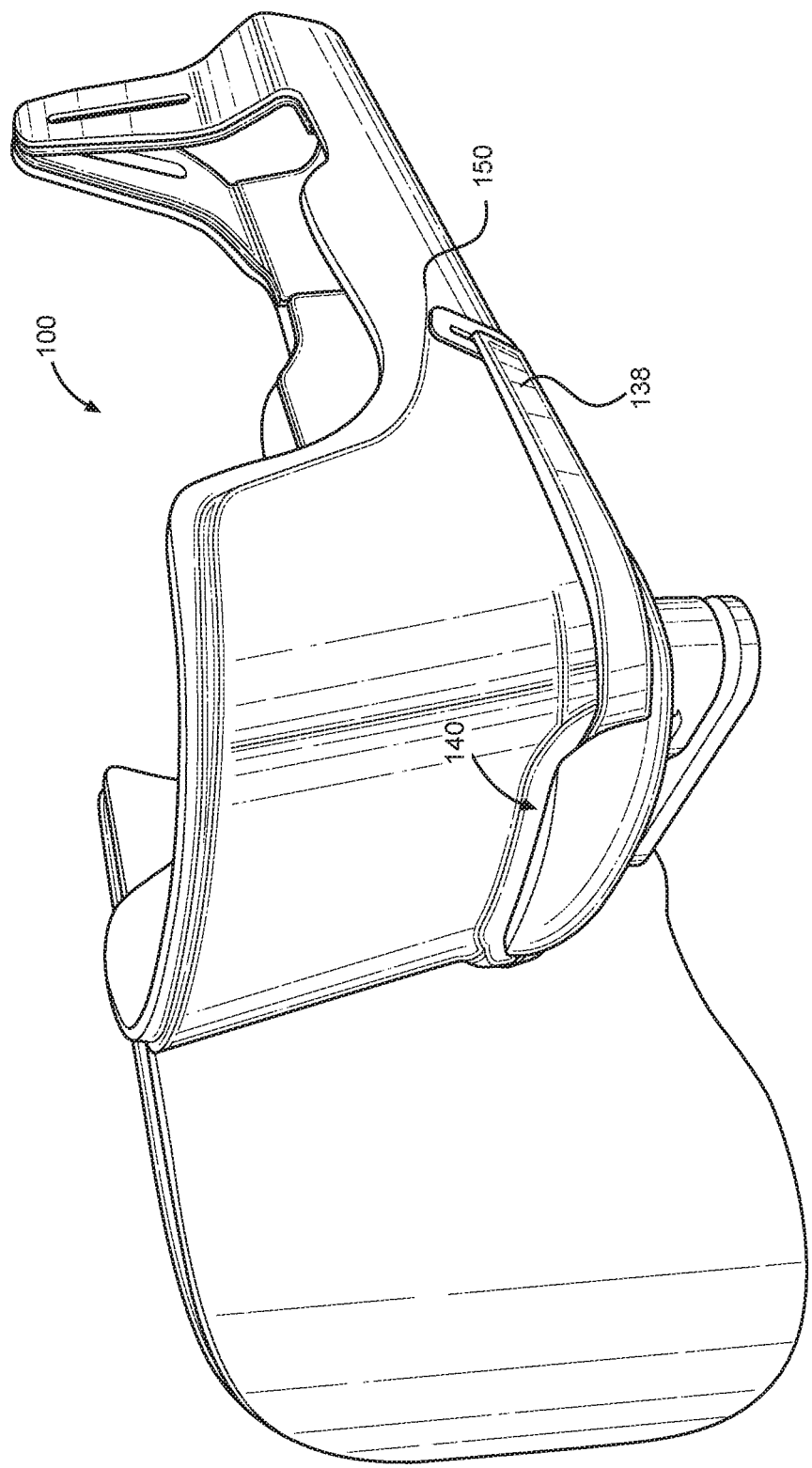
FIG. 1E is a rear perspective view of a portion of the example device of FIG. 1A.

According to some embodiments, the present disclosure is directed to a brace device or apparatus that address a condition of adhesive capsulitis, colloquially referred to as frozen shoulder (or any condition or injury causing loss of mobility of the shoulder). Adhesive capsulitis can result in a painful loss of range of motion. Braces described herein improve mobility range of motion to reduce pain and improve shoulder functioning. Adhesive capsulitis and corresponding loss of external rotation of the arm is due to contracture of rotator interval tissue of the shoulder. While treating adhesive capsulitis has been described, the device(s) of the present disclosure can be utilized to effective treat any condition resulting in shoulder stiffness.

Patients can be referred to physical therapy or home treatment when adhesive capsulitis or shoulder stiffness is diagnosed. Patients who fail to improve become surgical candidates.

The braces described herein can be used as an adjunct to typical physical therapy. In other embodiments it is envisioned that the braces can be utilized in a stand-alone capacity.

The braces described herein can also be utilized in a post-surgical setting to maintain mobility. Indeed, post-surgery adhesive capsulitis will begin to set in and re-tighten the shoulder unless intervention is initiated soon after surgery.

Some applications for the devices of the present disclosure allow for use as an adjunct in pre-operative settings in order to prepare an affected shoulder for surgery (e.g., reduce adhesions and/or other stiffness), and/or expedite post-operative recovery time.

Broadly, some embodiments described herein utilize dynamic stress to externally rotate the forearm of the patient while simultaneously maintaining the elbow of the arm in close proximity to the torso.

In general, the braces described herein effect this reduction in adhesive capsulitis by providing a force or stress onto an arm of an patient that causes external rotation of the arm (and specifically the forearm in some embodiments). Some embodiments incorporate means for providing dynamic stress, such as selective or gradually increasing of stress to stretch the shoulder as desired.

Some embodiments of braces described herein effectively places the forearm of a patient in an externally rotated position. This position is advantageous when it is desired to place the shoulder of the patient in an adducted (or neutral) position. Placing the shoulder in an adducted position is advantageous when the patient has suffered a shoulder injury or is recovering from one or more types of shoulder surgery.

The devices of the present disclosure can be utilized to lengthen, stretch, rotate, and/or otherwise manipulate a shoulder capsule (capsule and adjacent tissue(s)) in an affected shoulder connected to the forearm placed in a device of the present disclosure. To be sure, the shoulder capsule, when affected by adhesive capsulitis, will undergo any of thickening, fibrosis, and/or shrinkage due to inflammation and/or the development of adhesions. The devices of the present disclosure counteract these deleterious effects by dynamic stretching and lengthening of the shoulder capsule by rotation of the humorous caused by external rotation of the forearm, while the elbow of the patient is held in fixed position (distance) proximate the torso of the patient.

An example arm brace comprises a torso connection member, such as a belt, that is positioned on a torso of the patient. The torso connection member can be worn similarly to a belt and can be adjusted per the patient. The brace device also comprises an arm support member that couples with at least a forearm of a patient. The arm support member stabilizes the forearm of the patient.

In some embodiments the arm support member couples with the torso connection member in a pivoting manner to set an angle between the torso connection member and the arm support member, the angle being defined relative to a coronal plane of the patient.

Some embodiments of the present disclosure comprise a dynamic tensioning assembly/means that position a forearm of a patient in an externally rotated position. In some embodiments, the dynamic stressing means places a greater magnitude of force to rotate the forearm initially, but this force gradually decreases as the forearm moves into perpendicular relationship with the coronal plane of the patient (or vice-versa in other embodiments based on the type of dynamic tensioning assembly utilized).

FIGS. 1A-G illustrate an example dynamic brace device (referred to herein as "device 100"), constructed in accordance with the present disclosure. The device 100 comprises a torso member 102 (torso connection member), arm brace 104 (arm support member), and a dynamic tensioning assembly 106. In some embodiments, the torso member 102 is configured to rest against a hip HP and/or lower portion of a patient's torso T, as illustrated on a patient P. A body of the the torso member 102 is contoured to conform to the curvature of the torso T, around or proximate the iliac crest IC of the patient P. The body of the torso member 102 matches the natural curvature of the patient's torso T that typically provides a curvature above the iliac crest IC.

The torso member 102 provides a means of support for both the arm brace 104. When the patient P places their forearm FA in the arm brace 104, the weight of the arm will rest against the patient's torso T through the torso member 102.

A location of the torso member 102 relative to the torso T results in alignment with a natural position of the elbow relative to the torso when the arm is in a relaxed position extended down the side of the torso.

In one or more embodiments, the torso member 102 comprises one or more securement members 108 and 110. Additional or fewer securement members can be utilized. In various embodiments, the securement members 108 and 110 are adjustable straps or belts that allow the device 100 to be secured around patients of varying size and shape.

A mechanical linkage 111 couples the torso member 102 and the arm brace 104. In some embodiments, the mechanical linkage 111 comprises an upper armature 112 and a lower armature 114. The arm brace 104 is pivotally coupled to the upper armature 112 using a pivoting member 116. In some embodiments, the lower armature 114 can be removed. According to some embodiments, the arm brace 104 is pivotally coupled to the upper armature 112 using any means that allows for pivoting such as a pin or shaft extending through a cylinder of the pivoting member 116.

In some embodiments, the upper armature 112 and lower armature 114 are sized to allow the elbow E of the patient P to be placed in close proximity to the torso T of the patient P. Preferably, the elbow E of the patient P is located as close to the torso T, and the torso member 102 as possible. Maintaining the elbow E in close proximity to the torso T ensures that proper shoulder capsule SC movement is preserved during external rotation of the forearm FA of the patient P.

In other embodiments, additional dynamic or pivoting force can be induced when the pivoting member 116 comprises a torsion spring (or other torsion generating member) that can cause the arm brace 104 to internally and/or or externally rotate, as desired. Aspects of internal/external rotation of the arm will be discussed in greater detail below, although in general, the dynamic tensioning assembly 106 functions to cause the arm brace 104 to externally rotate and the pivoting member 116 can exert a torsion force that causes the arm brace 104 to internally rotate. When used in combination, these opposing forces can allow the patient to exercise their shoulder capsule by externally or internally rotating their forearm. When the patient is internally rotating the forearm, the dynamic tensioning assembly 106 resists the internal rotation, whereas when the patient is externally rotating their forearm, the pivoting member 116 resists the external rotation. These resistive forces for both internal and external movements allow the patient to exercise the shoulder capsule in two different directions. If only the dynamic tensioning assembly 106 is utilized, external rotation of the forearm is not resisted, only internal rotation, and vice versa if only the pivoting member 116 (such as a torsion spring is utilized).

According to some embodiments, the arm brace 104 is a cradle that receives the arm of the patient P. The arm brace 104 comprises an elbow and upper arm retaining portion 118 and a forearm retaining portion 120. In some embodiments, the arm brace 104 comprises a proximal grip 122 that can be gripped by a hand H of the patient P. In some embodiments, a length of the forearm retaining portion 120 can be increased or decreased using an adjustment assembly 124. The adjustment assembly 124 comprises a track 126 and locking nut 128 cooperate that that allow the proximal grip 122 to extend proximally or retract distally (towards the elbow E) to accommodate forearms of varying length. In operation, the locking nut 128 is loosened allowing the proximal grip 122 to slidably translate along the track 126. When in a desired position, the locking nut 128 can be tightened to secure the proximal grip 122 in position.

In general, the proximal grip is slidably extendable to selectively vary a length of a forearm retaining portion of the forearm support member.

In some embodiments, the proximal grip 122 comprises a pair of grip handles 130 and 132 that are spaced apart from one another. Each of the grip handles 130 and 132 can be used depending on an orientation of the device 100 (if being used on the right side or the left side of the torso T). When the patient P is using the device 100 on their right arm, grip handle 130 is utilized. The opposite grip handle is used when the device 100 is arranged for left arm use.

Turning now to the dynamic tensioning assembly 106. In some embodiments, the dynamic tensioning assembly 106 comprises a dial tensioner 134, a cable 136 in combination with the dial tensioner 134, and a dynamic force member 138. In some embodiments, the dial tensioner 134 is mounted on capable of being mounted on the torso member 102 in a position that is accessible to a hand of an opposing arm of the patient P that is not positioned inside the arm brace 104. The cable 136 runs through the dial tensioner 134 and couples to a terminal end of the dynamic force member 138.

The dynamic force member 138 extends around the elbow and upper arm retaining portion 118 of the arm brace 104. In some embodiments, the dynamic force member 138 is inserted through a slot 140 fabricated into an outer surface of the elbow and upper arm retaining portion 118 of the arm brace 104 to prevent the dynamic force member 138 from slipping under the arm brace 104. An opposing terminal end of the dynamic force member 138 is provided with a clip 142 that cooperates with an anchor 144 disposed along an outer surface of the forearm retaining portion 120 of the arm brace 104. The clip 142 locks into the anchor 144.

In some embodiments, the dynamic force member 138 comprises an elastomeric cable or strap.

In operation, as the dial tensioner 134 is rotated, the cable 136 is coiled within the dial tensioner 134, causing the cable 136 to pull on the dynamic force member 138. Because the terminal end of the dynamic force member 138 is anchored to an outer surface 150 of the forearm retaining portion 120 of the arm brace 104, as the dial tensioner 134 is turned, the dynamic force member 138 is stretched, causing the forearm retaining portion 120 of the arm brace 104 to pivot about the pivoting member 116, causing the forearm retaining portion 120 of the arm brace 104 to externally rotate.

In more detail, tensioning of the dynamic force member 138 creates a force applied to the forearm retaining portion 120 of the arm brace 104 that causes the stretching or other manipulation of the shoulder capsule to reduce adhesive capsulitis in an affected shoulder.

With respect to the operation of the device 100 when being used by the patient P. The patient P will first don the device 100 by locating the torso member 102 appropriately on their torso T (near the iliac crest IC). Next, the patient will utilize the one or more straps 118/120 to secure the device 100 onto the patient P. Once secured, the patient can place their forearm FA into the arm brace 104. It will be understood that the natural or initial position of the device 100 will place the forearm FA in proximity to, or near, the front of the torso T. This places the device 100 in an acute angle X1 relative to a coronal plane $C_P$ of the torso T. To place dynamic tension on the forearm FA, the patient will begin to turn the dial tensioner 134 on the torso member 102, which causes the cable 136 to tension the dynamic force member 138. Pulling on the dynamic force member 138 will result in external rotation (as illustrated by the dotted line and arrow) of the forearm retaining portion 120 of the arm brace 104. As the dial tensioner 134 is turned, the force created by the dynamic tensioning assembly 106 will begin to translate the forearm retaining portion 120 the arm brace 104, moving the forearm retaining portion 120 of the arm brace 104 to a position that further away from the torso T and closer to an angle X2 that is substantially perpendicular/orthogonal to the coronal plane $C_P$ of the torso T.

In embodiments where the dynamic force member 138 is an elastic or resilient member, the elastic or resilient nature of the dynamic force member 138 allows the patient P to push or pull their forearm FA to exercise their shoulder joint S, reducing and/or eliminating adhesive capsulitis in the shoulder joint S. Ideally, the patient should seek to position their arm closer to angle X2 (see FIGS. 1B and 1G), but limitations on mobility can hamper this magnitude of movement. Thus, the patient can incrementally change their forearm angle between X1 and X2 (see FIGS. 1F and 1G) in various sessions or over a period of time using the device 100 to improve their range of motion and reduce adhesive capsulitis. At any position, the patient can achieve benefits of pushing or pulling against a force created by the dynamic force member 138.

It will also be understood that the dynamic tensioning assembly 106 creates a dynamic force that varies according to forearm angle. That is, when the forearm is located proximate angle X1, the force created by the dynamic tensioning assembly 106 are less than when the dynamic tensioning assembly 106 is used to place the forearm proximate angle X2. In other words, the dynamic tensioning assembly 106 exerts an incrementally increasing amount of force as the dial tensioner 134 is turned and as the arm brace transitions from X1 to X2. Again, the device 100 can be otherwise configured to create an incrementally decreasing range of force when transitioning from X1 to X2, rather than incrementally increasing Advantageously, the device 100, in operation, lengthens a shoulder capsule in an affected shoulder connected to the forearm. To be sure, the shoulder capsule, when affected by adhesive capsulitis, will undergo any of thickening, fibrosis, and/or shrinkage due to inflammation and/or the development of adhesions. The device 100 counteracts these deleterious effects by dynamic stretching and lengthening of the shoulder capsule by rotation of the humorous caused by external rotation of the forearm, while the elbow of the patient is held in fixed position proximate the torso of the patient.

In yet another advantage, the tensioning of the strap (e.g., dynamic force member 138) allows the patient to internally rotate or externally rotate the forearm support member (arm brace 104) to exercise the shoulder capsule. The strap resists the internal or external rotation of the forearm support member by the patient, allowing the patient to exercise the shoulder capsule. In some instances, if these exercises are performed pre-operatively, the patient may avoid surgery by reducing the adhesive capsulitis to such a degree that the shoulder capsule is rehabilitated.

In various embodiments, as illustrated in FIGS. 1B and 1C, the device 100 can comprise a shoulder strap 160. The shoulder strap 160 overlaps the non-affected shoulder (shoulder not connected to the arm placed in the device 100) and bears a portion of the weight of the device 100. The shoulder strap 160 can connect to the torso member 102.

In some embodiments, the device 100 comprises the arm brace 104 comprising several components such as the elbow and upper arm retaining portion 118 and forearm retaining portion 120. An anchor 144 (anchor location) is located on an outside surface of the forearm retaining portion. The retaining slot 140 is located on a rearward portion of the elbow and upper arm retaining portion.

In some embodiments, an extendable, proximal grip 121 is disposed on a terminal end of the elbow and upper arm retaining portion 118, and the extendable, proximal grip 121 is capable of sliding translation to adjust a length of the elbow and upper arm retaining portion 118. The extendable, proximal grip 121 further comprises a pair of spaced apart hand grips 130 and 132.

As noted above, the device 100 comprises the torso connection member 102 (torso member), and the torso member 102 can comprise a body contoured to mate with a portion of a side of a torso T of the patient at approximately an iliac crest IC of the patient P.

The n torso member 102 comprises one or more securement members (108 and 110) coupled to the body of the torso member 102. The one or more securement members are each configured to overlap an opposing side of the torso of the patient to secure the torso connection member on the torso.

In some embodiments the device 100 includes a linkage that couples the elbow and upper arm retaining portion with the torso connection member in such a way that the elbow of the patient is next to the torso of the patient. The elbow and upper arm retaining portion is pivotally coupled with the linkage, as noted above. This can include a dynamic pivoting (such as a torsion spring) or a free rotating pivot.

A dial tensioner is disposed on a forward portion of the body so as to be reachable by an opposing hand of the patient that is not placed in the elbow and upper arm retaining portion.

In some embodiments, a resilient strap is coupled with the dial tensioner at one end, the resilient strap coupling with the forearm retaining portion using a clip that releaseably connects with the anchor location, the resilient strap extending through the retaining slot.

It will be understood that when the patient places their arm in the arm brace and rotates the dial tensioner, the arm brace pivots to externally rotate a forearm while the elbow is maintained in a fixed position, resulting in stretching of a shoulder capsule of a shoulder of the patient, the resilient strap providing a dynamic force that can be resisted against by the patient. In some embodiments, the device 100 includes a shoulder strap that overlaps a non-affected shoulder, the shoulder strap connected on both its ends to the body of the torso connection member.

FIGS. 2A-D collectively illustrate another example dynamic brace device (referred to herein as "device 200"), constructed in accordance with the present disclosure. The device 200 is similar in construction to that of the device 100 of FIGS. 1A-G, with respect to the torso member 202 and the arm brace 204, but rather than using a dynamic tensioning assembly that comprises a dynamic force member, the device 200 comprises a dynamic tensioning assembly 206 that comprises a series of belt or chain driven components in order to induce pivoting rotation of the arm brace 204 relative to the torso member 202.

The device of FIGS. 2A-D can include any of the securement straps disclosed relative to FIGS. 1A-G.

In some embodiments, the dynamic tensioning assembly 206 comprises a gear assembly comprising a geared torsion spring 208 and a tensioning dial 210 that is mechanically coupled with the geared torsion spring 208.

In general, wherein turning of the tensioning dial 210 causes the forearm support member (arm brace 204) to externally rotate as the geared torsion spring 208 is loaded. In more detail, the geared torsion spring 208 comprises a keyed hub 212, a rim 214, and a plurality of elastomeric spokes 217 that extend between the keyed hub 212 and the rim 214.

The geared torsion spring 208 is mounted on a keyed shaft 216 that extends from a linkage 218 associated with the torso member 202. In some embodiments, the keyed shaft 216 is fixed in position. The keyed hub 212 of the geared torsion spring 208 slides over the keyed shaft 216.

The rim 214 comprises a plurality of teeth 220 that are disposed on the outer surface of the rim 214. Similarly, the tensioning dial 210 comprises a toothed gear 222. In one or more embodiments, a tracked belt 224 couples the rim 214 of the geared torsion spring 208 with the toothed gear 222 of the tensioning dial 210. Thus, as the tensioning dial 210 is rotated, a corresponding rotation of the torsion spring 208 occurs. Because the rim 214 and the keyed hub 212 of the geared torsion spring 208 are connected to one another via the plurality of elastomeric spokes 217, and the keyed hub 212 is held in fixed position on the keyed shaft 216, torsion force begins to build in the plurality of elastomeric spokes 217 as the tensioning dial 210 is rotated. This also causes the arm brace 204 to pivot at the linkage 218 and externally rotate.

In sum, the load applied to the geared torsion spring creates a force applied to the forearm support member (arm brace 204) that causes the stretching of the shoulder capsule.

If the patient desires to lock the arm brace 204 in its angled position, a locking member 226 can be engaged. The locking member 226 retains the forearm support member (arm brace 204) at a selected angle position and the geared torsion spring 208 with a selected loading. The locking member 226 translates forwardly to engage with the toothed gear 222 of the tensioning dial 210, preventing the tensioning dial 210 from rotational movement.

Figure 2A:
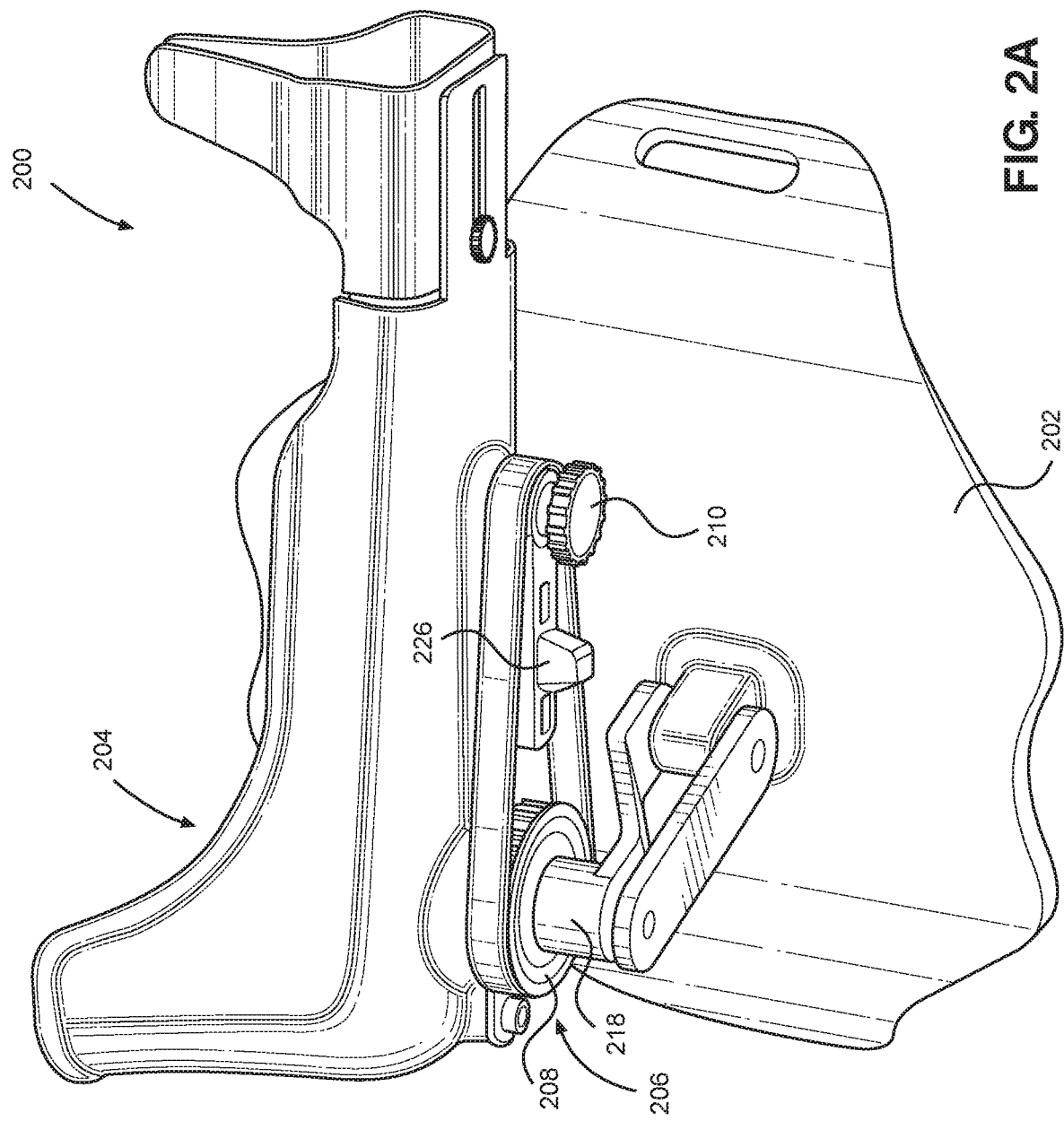
FIG. 2A is a partial perspective view of another example device of the present disclosure comprising a gear-driven dynamic force assembly.
Figure 2B:
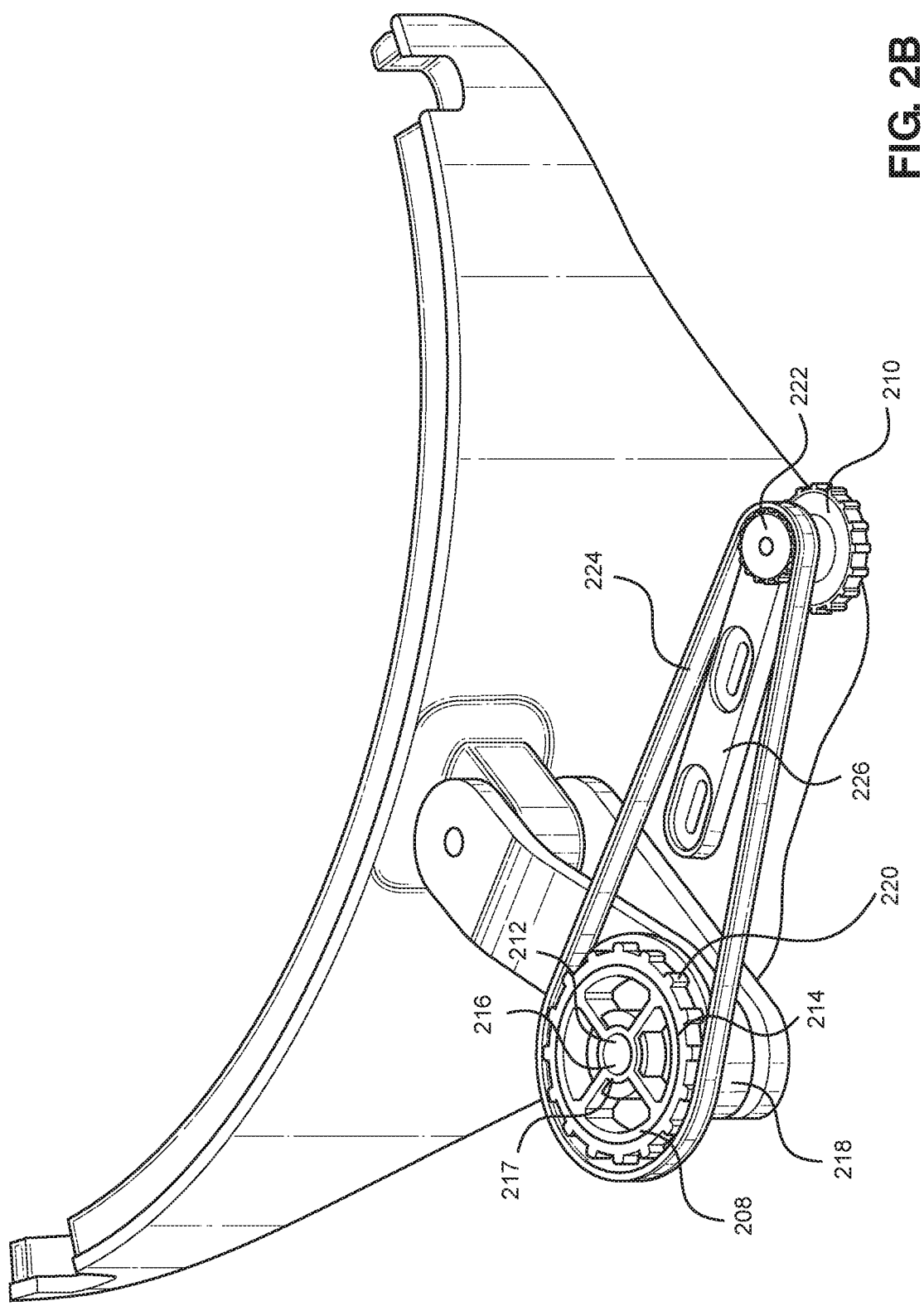
FIG. 2B is a partial perspective view of the gear-driven dynamic force assembly.
Figure 2C:
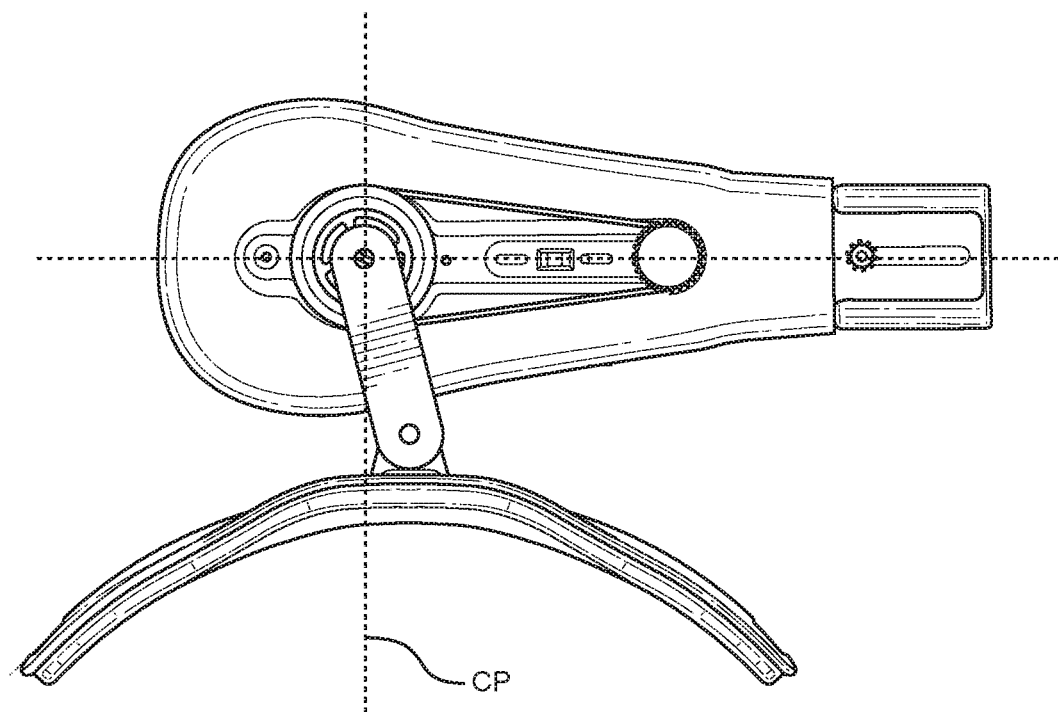
FIGS. 2C and 2D collectively illustrate device movement between an initial position (FIG. 2D) and an externally rotated position (FIG. 2C).
Figure 2D:
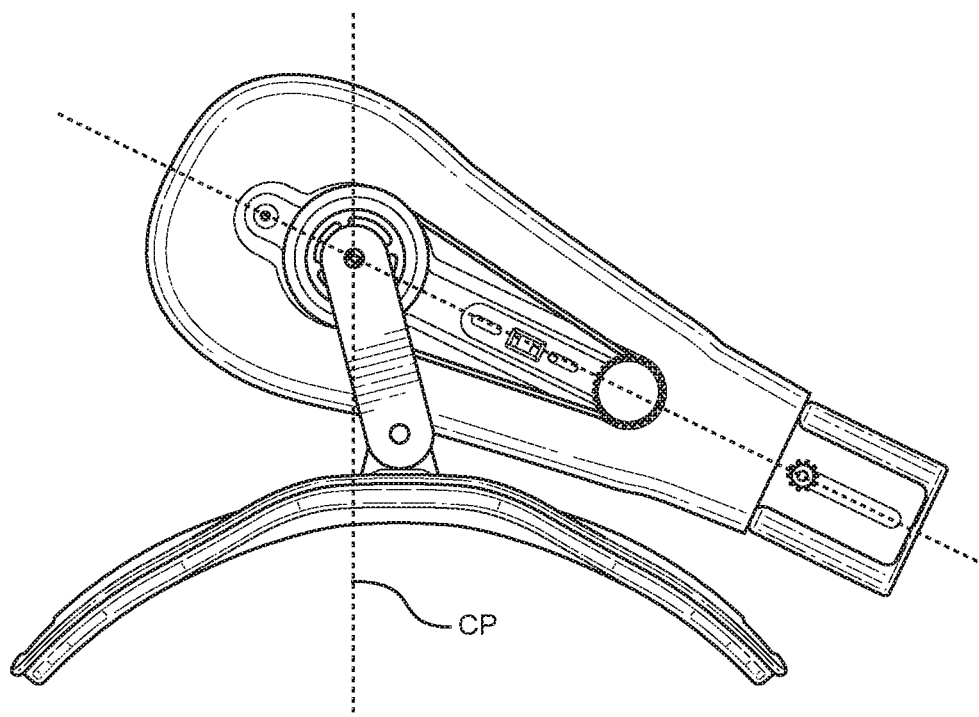

FIGS. 2C-D illustrate various positions of the device 200, where in FIG. 2C the device 200 positions the arm brace 204 proximate the torso of the patient, while the position of FIG. 2D illustrates the device 200 in a position where the arm brace 204 is substantially perpendicular to the coronal plane $C_P$ of the patient.

FIG. 3 illustrates an example embodiment of a brace device 310 constructed in accordance with the present disclosure. The brace device 310 comprises generally a torso member 312, an arm sling 316, and a dynamic tensioning assembly 318. A coronal plane $C_P$ is illustrated for reference.

The torso member 312 can comprise a belt or similar structure that securely wraps a torso 320 at any position. The arm sling 316 can comprise a sleeve type sling in one embodiment. In another embodiment the arm sling 316 can comprise one or more straps such as strap 322 that secures to a forearm 324.

The dynamic tensioning assembly 318 comprises a pre-tensioned or resiliently biased member that couples with the torso member 312 and the arm sling 316. The shape of the dynamic tensioning assembly 318 is configured to retain an elbow 326 in close proximity to the torso 320. In some embodiments, the dynamic tensioning assembly 318 provides a rotating force that causes external rotation of the forearm 324. In one embodiment the dynamic tensioning assembly 318 places the forearm 324 into a position that is substantially perpendicular to the coronal plane $C_P$.

Advantageously, the patient can push against the dynamic tensioning assembly 318 to exercise the arm and associated shoulder to reduce the likelihood that adhesive capsulitis will occur or reoccur in the shoulder. The dynamic tensioning of the dynamic tensioning assembly 318 will force the forearm 324 into external rotation when the patient stops pushing against the dynamic tensioning assembly 318. The dynamic tensioning assembly 318 can be manufactured from any desired materials including, but not limited to plastics, polymers, metals, alloys, composite materials, natural materials such as wood, and other materials that can provide the aforementioned dynamic pre-tensioning features described herein.

FIG. 4 illustrates an example embodiment of a brace device 400 constructed in accordance with the present disclosure. The device 400 generally comprises a torso member 402, an elbow securement member 404, an arm sling 406, and a dynamic tensioning assembly 408. A coronal plane $C_P$ is illustrated for reference.

The torso member 402 can comprise a belt or similar structure that securely wraps a torso 410 at any position, but in some embodiments in alignment with a natural position of the elbow relative to the torso when the arm is in a relaxed position extended down the side of the torso. The elbow securement member 404 can comprise a strap or loop of material that cooperates with the belt to maintaining the elbow of the arm in close proximity to the torso. The elbow securement member 404 can comprise any suitable means for maintaining the elbow of the arm in close proximity to the torso.

The arm sling 406 is configured to receive and retain a forearm and/or other portions of an arm 412 of the patient.

The dynamic tensioning assembly 408 comprises a buckle or other receiver 414 mounted onto the arm sling 406, and a tensioning strap 416. The arm sling 406 is mounted onto a portion of the arm sling 406 that is proximate an outside surface of the arm sling 406.

The tensioning strap 416 is secured to the torso member 402 for anchoring at one end. A terminal end 418 of the tensioning strap 416 is looped around or through the receiver (such as a buckle) 414 and wraps back around the rear side of the torso. As the patient pulls on the terminal end 418 of the tensioning strap 416 will exert a force that externally rotates the forearm of the patient while the elbow securement member 404 simultaneously maintains the elbow of the arm in close proximity to the torso. The external rotation places the arm into a substantially perpendicular relationship to the coronal plane $C_P$ in some embodiments. In other embodiments, the dynamic tensioning assembly 408 places the arm at any desired angular position relative to the coronal plane $C_P$, which can include angles that are greater or less than perpendicular to the coronal plane $C_P$.

The terminal end 418 is provided with hook and loop fasteners or another securement means for allowing the terminal end 418 to securely contact the torso member 402 to retain the terminal end 418 in a desired position to maintain external rotation forces on the forearm.

The torso member 402 can also comprise tensioning indicia 420 printed on a front portion thereof. The tensioning indicia 420 allow a user to set the dynamic tension of the device 400 accurately for every use.

In some embodiments, the torso member 402 and elbow securement member 404 function as a single unitary unit. The torso member 402 and elbow securement member 404 can be a single loop or belt, for example.

Figure 5:
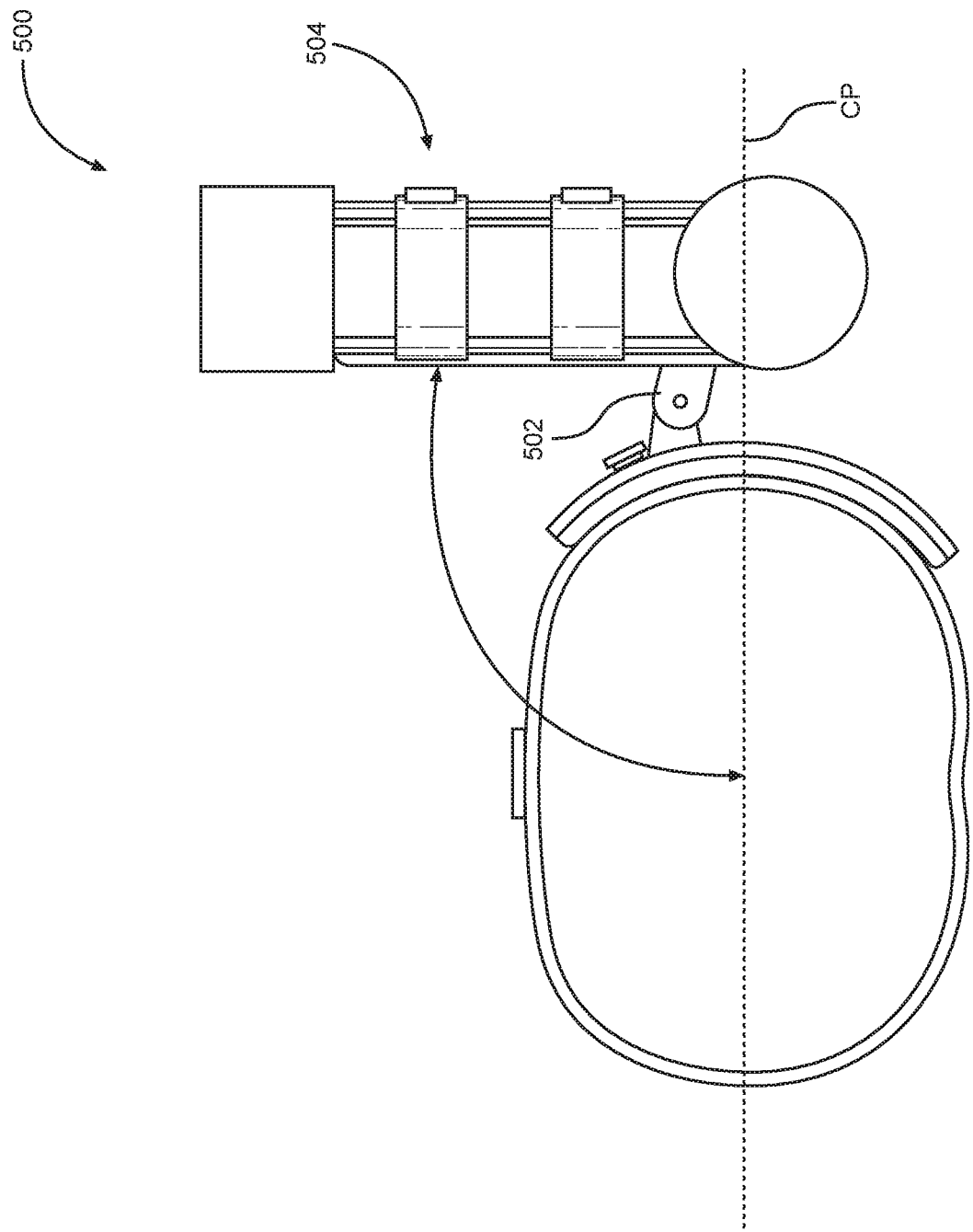
FIG. 5 is a top-down perspective view of another embodiment of a device of the present disclosure having a dynamic tensioning element in the form of a pre-tensioned hinge or torsion spring.

FIG. 5 is another embodiment of a brace device 500 constructed in accordance with the present disclosure. The brace device 500 utilizes a tensioned pivoting member 502, such as a pre-tensioned hinge or spring (such as a torsion spring) that externally rotates an arm brace 504 into a desired position, such as substantially perpendicular to the coronal plane $C_P$.

Figure 6:
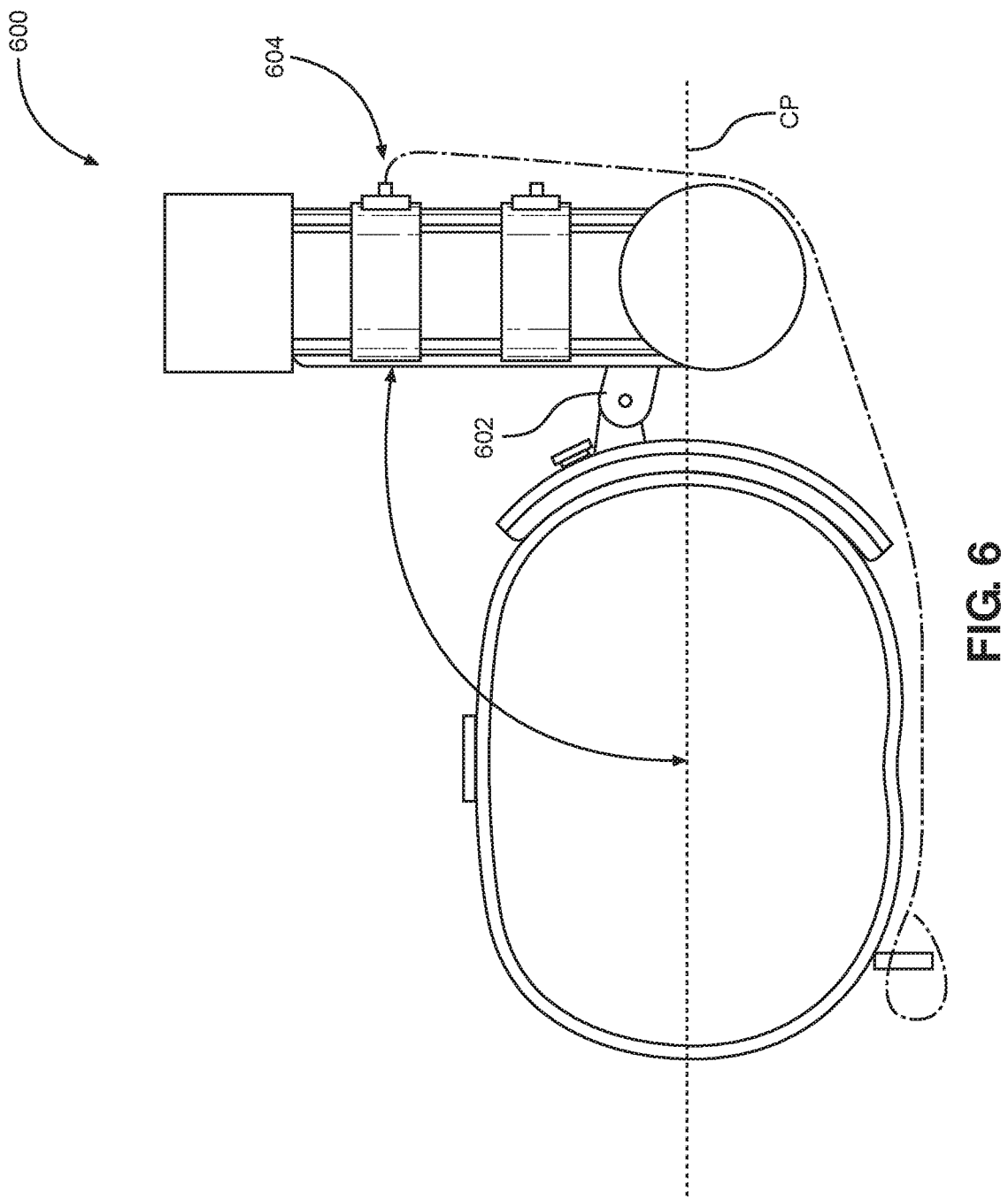
FIG. 6 is a top-down perspective view of another embodiment of a device of the present disclosure having a dynamic tensioning element in the form of a pre-tensioned hinge or torsion spring, in combination with a tensioning strap.

FIG. 6 illustrates another example embodiment of a brace device 600 that includes a tensioned pivoting member 602 and a tensioning strap 604 (as well as a receiver or buckle similar to the embodiment of FIG. 4).

Figure 7:
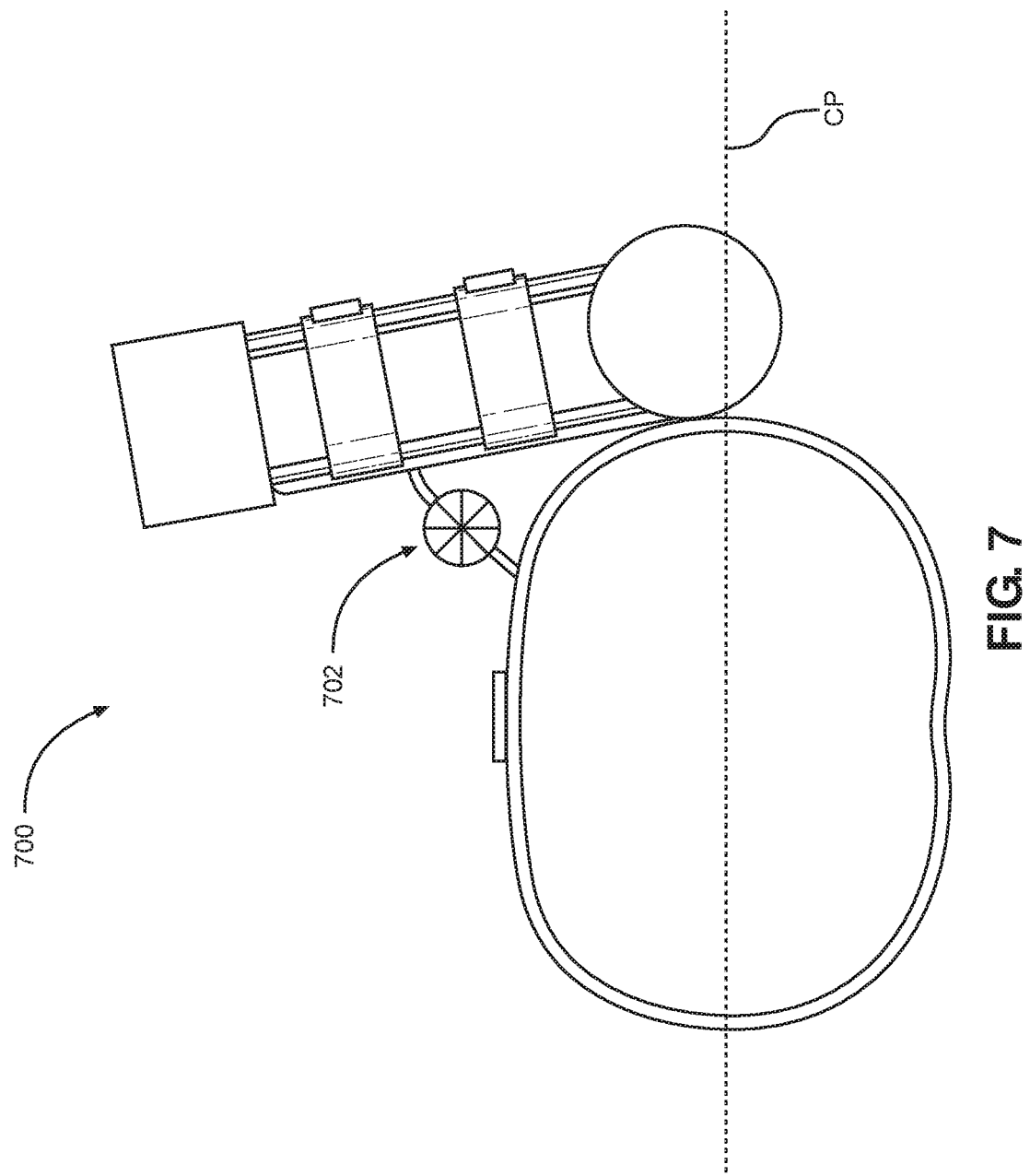
FIGS. 7 and 8 collectively illustrate another example device of the present disclosure that comprises a compass-style dynamic tensioning element.
Figure 8:
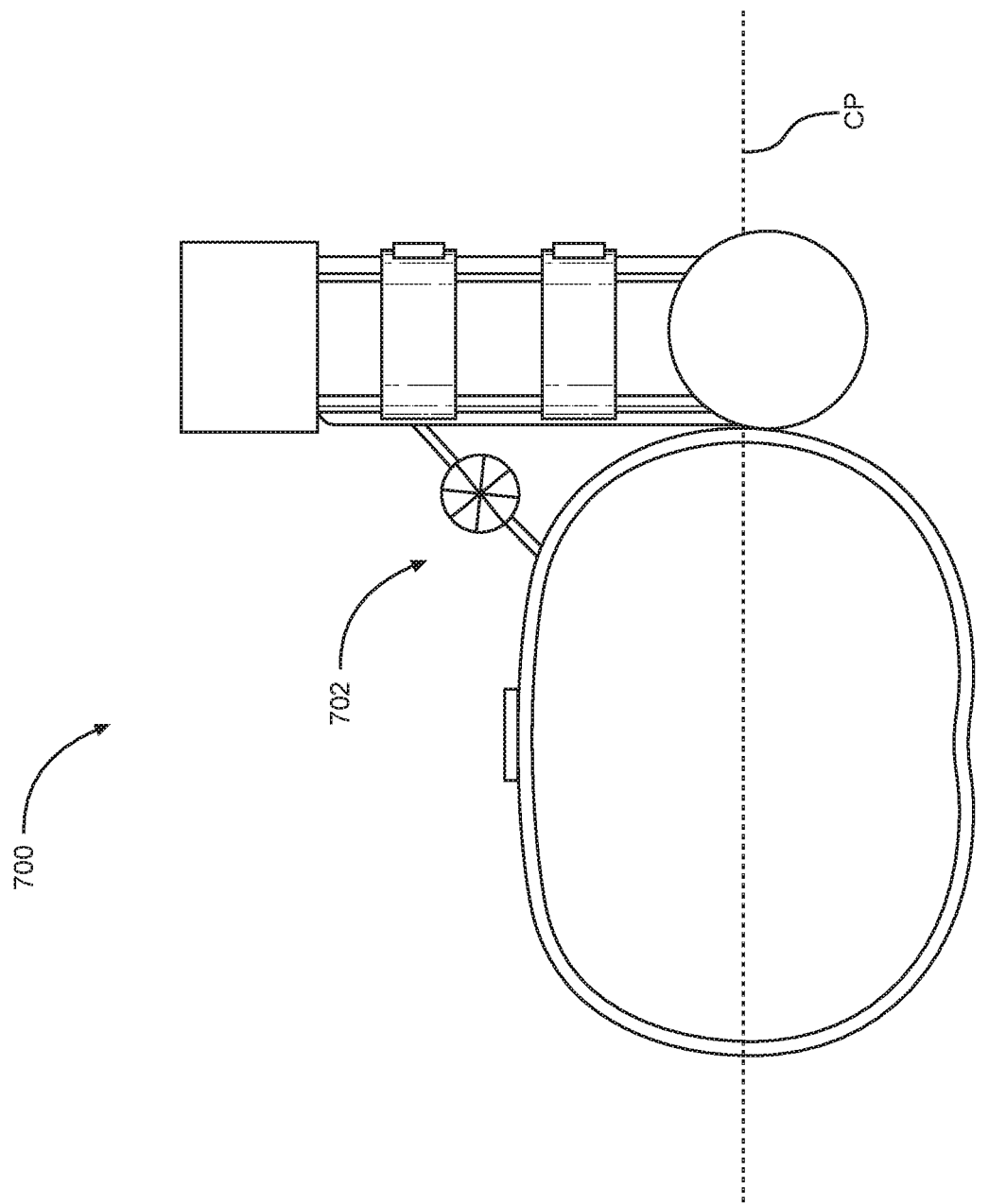

FIGS. 7 and 8 collectively illustrate another example embodiment of a brace device 700 that includes a compass type force member 702 that provides dynamic forces to externally rotate the forearm into position relative to the coronal plane $C_P$.

Figure 9:
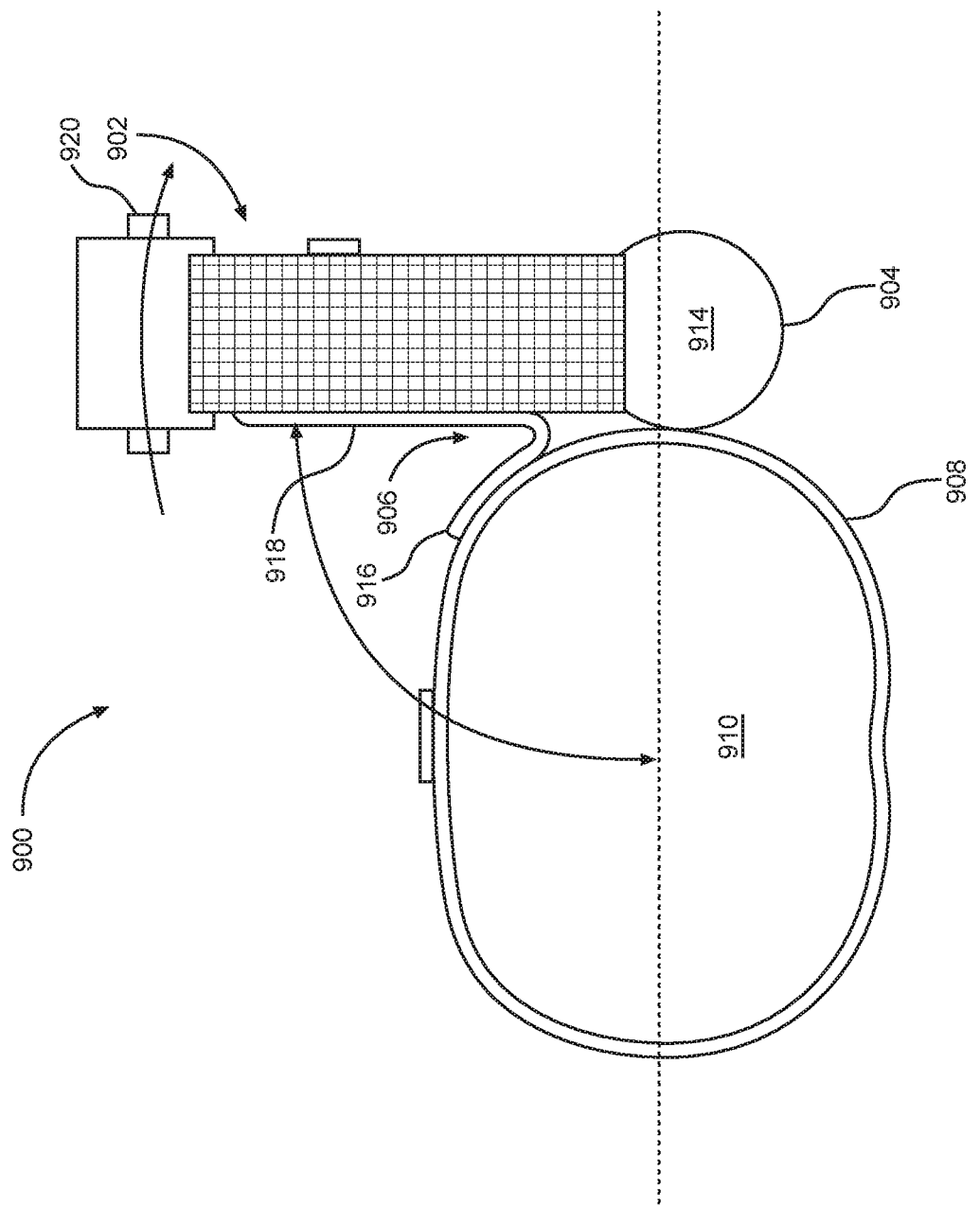
FIG. 9 is a top-down perspective view of another embodiment of a device of the present disclosure, comprising a therapeutic handle for exercise.

FIG. 9 illustrates another example embodiment of a brace device 900 that includes an arm brace 902, an elbow positioning member 904, and a dynamic tensioning member 906. The elbow positioning member 904 includes a belt 908 that wraps around a torso 910 and a loop or strap 912 that wraps around an elbow 914. The belt 908 and loop or strap 912 are coupled together in some embodiments.

In one embodiment the dynamic tensioning member 906 comprises a substantially V-shaped member that exerts dynamic forces on the arm brace 902 to externally rotate the forearm of the patient. A portion 916 of the dynamic tensioning member 906 contacts the torso 910 and a portion 918 of the dynamic tensioning member 906 contacts the arm brace 902 (e.g., forearm). The patient can also compress the portion 916 and portion 918 towards one another. Resiliency of the dynamic tensioning member 906 causes the portions 916 and 918 to spring back to a desired externally rotated forearm position when the patient is not exerting compressive forces on the dynamic tensioning member 906. Again, this dynamic tensioning member 906 can be constructed from materials that allow the dynamic tensioning member 906 to exert a greater magnitude of force to externally rotate the forearm when the portions 916 and 918 are closer together (e.g., at an angle where the forearm is less than perpendicular to the coronal plane), where this force decreases in magnitude as the forearm is externally rotated closer to perpendicular with the coronal plane.

An example detachable therapy handle is illustrated as 920. The therapy handle can be coupled mechanically to the arm brace 902 or other portion of the brace device 900. The handle allows the patient to grip and exert force against the dynamic tensioning member 906 to exercise the shoulder joint of the shoulder associated with the arm in the brace device 900.

While aspects of the present disclosure have been disclosed for treating an affected area of a patient, such as a shoulder affected with adhesive capsulitis, the teachings of the present disclosure are not so limited. The present disclosure can be extended and adapted to treating other conditions that are similar in nature to adhesive capsulitis, and the devices disclosed herein can be adapted for use on other joints such as knees, wrists, elbows, ankles, and other similar structures.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "mechanically connected," etc., are used interchangeably herein to generally refer to the condition of being physically connected. If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A device, comprising:
   a torso connection member securable to a torso of a patient;
   a forearm support member that is configured to couple with at least a forearm of a patient the forearm support member being pivotally coupled to the torso connection member; and
   a dynamic tensioning assembly that is configured to externally rotate the forearm support member and selectively set an angle so as to stretch a shoulder capsule affected with adhesive capsulitis so as to reduce the adhesive capsulitis, the dynamic tensioning assembly comprising an elastomeric or resilient strap that couples to an outer surface of the forearm support member, a dial tensioning member, and a cable extending through the dial tensioning member and coupled to the elastomeric or resilient strap, wherein rotation of the dial tensioning member causes the cable to tension the elastomeric or resilient strap, resulting in the external rotation of the forearm support member, wherein tensioning of the elastomeric or resilient strap creates a force applied to the forearm support member that is configured to cause the stretching of the shoulder capsule.

2. The device according to claim 1, wherein the forearm support member comprises a proximal grip that is configured to receive a hand of the patient, the proximal grip comprising two grip handles.

3. The device according to claim 2, wherein the proximal grip is slidably extendable to selectively vary a length of a forearm retaining portion of the forearm support member.

4. The device according to claim 1, wherein the tensioning of the elastomeric or resilient strap is configured to allow the patient to internally rotate or externally rotate the forearm support member to exercise the shoulder capsule, the elastomeric or resilient strap resisting the internal or external rotation of the forearm support member by the patient.

5. The device according to claim 1, further comprising a mechanical linkage that spaces the forearm support member and the torso connection member, the mechanical linkage comprising an upper armature and a lower armature, the forearm support member being pivotally coupled to the upper armature.

6. The device according to claim 1, further comprising a resiliently biased coupling between the torso connection member and the forearm support member.

7. The device according to claim 1, wherein the torso connection member comprises:
   a contoured body portion that is configured to rest proximate an iliac crest and hip of the patient; and
   a belt that is configured to secure the contoured body portion to the torso.

8. A device that is configured to place an associate shoulder of a patient in an adducted position that stretches a shoulder capsule, the device comprising:
   a forearm support member that is configured to secure to at least a forearm of a patient; and
   a torso connection member that is positioned and is configured to secure proximate an iliac crest of the patient;
   wherein the forearm support member couples with the torso connection member in such a way that an elbow of the patient is configured to be proximate to a torso of the patient; and
   wherein the forearm support member and a coronal plane of the patient is approximately normal to one another using a dynamic tensioning assembly, the dynamic tensioning assembly comprising an elastomeric or resilient strap that couples to an outer surface of the forearm support member, a dial tensioning member, and a cable extending through dial tensioning member and coupled to the elastomeric or resilient strap, the dial tensioning member being placed on the torso connection member, wherein rotation of the dial tensioning member causes the cable to tension the elastomeric or resilient strap, resulting in external rotation of the forearm support member, wherein tensioning of the elastomeric or resilient strap creates a force applied to the forearm support member that is configured to cause the stretching of the shoulder capsule.

9. A device, comprising:
   an arm brace comprising:
      an elbow and upper arm retaining portion;
      a forearm retaining portion;
      an anchor location on an outside surface of the forearm retaining portion;
      a retaining slot located on a rearward portion of the elbow and upper arm retaining portion; and
      an extendable, proximal grip disposed on a terminal end of the elbow and upper arm retaining portion, the extendable, proximal grip capable of sliding translation to adjust a length of the elbow and upper arm retaining portion, the extendable, proximal grip further comprising a pair of spaced apart hand grips;
   a torso connection member comprising:
      a body contoured and configured to mate with a portion of a side of a torso of a patient at approximately an iliac crest of the patient; and
      one or more securement members coupled to the body, the one or more securement members configured to overlap an opposing side of the torso of the patient to secure the torso connection member on the torso;
   a linkage that is configured to couple the elbow and upper arm retaining portion with the torso connection member in such a way that an elbow of the patient is next to the torso of the patient, wherein the elbow and upper arm retaining portion is pivotally coupled with the linkage;
   a dial tensioner that is disposed on a forward portion of the body configured to be reachable by an opposing hand of the patient that is not placed in the elbow and upper arm retaining portion;
   a resilient strap that is coupled with the dial tensioner at one end, the resilient strap coupling with the forearm retaining portion using a clip that releaseably connects with the anchor location, the resilient strap extending through the retaining slot; and
   wherein when the patient places their arm in the arm brace and rotates the dial tensioner, the arm brace pivots to externally rotate a forearm while the elbow is maintained in a fixed position, and is configured to result in stretching of a shoulder capsule of a shoulder of the patient, the resilient strap providing a dynamic force that can be resisted against and moved by internal rotation of the forearm by the patient causing the resilient strap to stretch;
   a shoulder strap that is configured to overlap a non-affected shoulder, the shoulder strap connected on both ends of the shoulder strap to the body of the torso connection member.

* * * * *